(12) United States Patent
Edwards et al.

(10) Patent No.: US 6,610,149 B2
(45) Date of Patent: Aug. 26, 2003

(54) APPARATUS FOR TREATING DENTURES

(75) Inventors: Mark Ieuan Edwards, Sunbury-Thames (GB); Iain Allan Hughes, Surrey (GB)

(73) Assignee: The Procter & Gamble Company, Cincinnati, OH (US)

( * ) Notice: Subject to any disclaimer, the term of this patent is extended or adjusted under 35 U.S.C. 154(b) by 210 days.

(21) Appl. No.: 09/780,806

(22) Filed: Feb. 9, 2001

(65) Prior Publication Data

US 2002/0157985 A1 Oct. 31, 2002

Related U.S. Application Data

(62) Division of application No. 09/341,730, filed as application No. PCT/US98/00700 on Jan. 14, 1998, now Pat. No. 6,217,933.

(30) Foreign Application Priority Data

Jan. 16, 1997 (GB) .............................................. 9700841
Nov. 5, 1997 (GB) .............................................. 9723534

(51) Int. Cl.$^7$ ............................................. B05C 19/02
(52) U.S. Cl. ....................................... 118/423; 118/429
(58) Field of Search ................................ 118/423, 429, 118/501; 427/2.29, 430.1, 353, 368, 387; 106/35; 252/188.2, 186.1; 424/466, 49, 52; 134/135, 137; 510/116, 400, 367, 378; 422/301, 300, 261, 28, 32, 37

(56) References Cited

U.S. PATENT DOCUMENTS

| | | |
|---|---|---|
| 3,607,759 A | 9/1971 | Barth |
| 3,793,211 A | 2/1974 | Kohlhepp et al. |
| 4,155,868 A | 5/1979 | Kaplan et al. |
| 4,336,816 A | 6/1982 | Horz et al. |
| 4,724,855 A | 2/1988 | Jackson et al. |
| 4,994,593 A | 2/1991 | Lin et al. |
| 5,078,988 A | 1/1992 | Lin et al. |
| 5,154,915 A | 10/1992 | Weber et al. |
| 5,188,822 A | 2/1993 | Viccaro et al. |
| 5,427,770 A | 6/1995 | Viccaro et al. |
| 5,665,374 A | 9/1997 | Hill et al. |
| 5,759,523 A | 6/1998 | Hughes et al. |
| 5,827,505 A | 10/1998 | Hughes et al. |
| 5,856,282 A | 1/1999 | Hughes |
| 6,008,171 A | 12/1999 | Hughes et al. |
| 6,024,891 A | 2/2000 | Hughes |
| 6,123,950 A | 9/2000 | Hughes |
| 6,153,567 A | 11/2000 | Hughes |

FOREIGN PATENT DOCUMENTS

| | | |
|---|---|---|
| EP | 0373688 | 6/1990 |
| EP | 0398177 | 11/1990 |
| EP | 0528457 | 2/1993 |
| WO | WO7900454 | 7/1979 |

OTHER PUBLICATIONS

US 6,132,700, 10/2000, Hughes (withdrawn).
Pastour et al., "Water in Oil Emulsions for Cosmetic or Pharmaceutical Use", Chemical Abstracts, vol. 121, No. 18, (Oct. 1994). pp. 524, col. 1, Abstract No. 212641B.

*Primary Examiner*—Brenda A. Lamb
(74) *Attorney, Agent, or Firm*—Dinsmore & Shohl LLP

(57) ABSTRACT

Denture baths comprise an outer container for containing an aqueous composition; means for supporting a denture in the container, which means allow the denture to be immersed in the aqueous composition; and an aqueous composition. The aqueous composition comprises a polymeric coating agent having a surface tension in 0.1% aqueous solution of less than 37 mNm$^{-1}$ and a weight average molecular weight of 1,000 or greater. In addition, the denture baths comprise a means for passing the denture through an interface of the aqueous composition with the surrounding air, the means being selected from means for draining the composition from a position beneath the denture and means for lifting the denture through the interface.

17 Claims, 2 Drawing Sheets

APPARATUS FOR TREATING DENTURES

RELATED APPLICATIONS

This application is a divisional of U.S. Application Ser. No. 09/341,730 filed on Jul. 15, 1999, now U.S. Pat. No. 6,217,933, which is a 35 USC 371 filing of PCT/US98/00700 filed on Jan. 14, 1998, which claims priority from GB 9723534.5 filed Nov. 5, 1997 and GB 9700841.1 filed Jan. 16, 1997.

TECHNICAL FIELD

The present invention relates to a method for applying a polymeric, surface coating to dentures and similar articles that are placed within the mouth, such as orthodontic brackets and the like. In particular, the invention relates to the application of a polymeric, silicone coating to dentures by passing the denture through an air-solution interface at which the polymer is concentrated. The coating resists the growth of plaque on the denture.

BACKGROUND

Tablets and powders for cleansing dentures and the like are well known in the art. A common method for using such a product is to place a tablet and a denture in a beaker and then to fill the beaker with water, thereby dissolving the tablet and creating a cleansing bath in which the denture is immersed for a period of from a few minutes to several hours. The aim of a denture cleanser product is to clean the denture as fully and as quickly as possible and especially to remove the accumulation of plaque, mucilaginous and bacterial deposits which collect while the denture is being worn. To wear a denture which has not been completely cleaned of plaque and bacterial deposits is not only unhygienic but can also within a short space of time result in a detrimental effect on the mucous membrane. Consequently, agents which can reduce the adhesion of bacteria to the cleaned denture and thus retard plaque build-up have also been described in the art. Many silicones are suitable for this purpose as described, for example, in WO 96/19563 and WO 96/19191. WO 96/16630 also describes the use of fluorocarbon containing polymers for coating hard tissue and surfaces of the oral environment, including dentures and the like.

To be fully effective, such coatings must be applied uniformly over the whole denture surface. It has now surprisingly been found that the effectiveness of application of such coatings can be enhanced by careful control of the passage of the denture through the air interface of an aqueous bath comprising a polymeric coating agent. In particular, it has been found that coating is enhanced if the denture is withdrawn through the air interface or if the bath is drained from below such that the interface passes over the denture, rather than, for example, decanting the bath contents by tipping. Whilst not wishing to be bound by theory, it is believed that an important factor may be the avoidance of an increase in the surface area of the interface, which could lead to the surface pressure at the interface dropping, whilst the denture passes through it.

Accordingly, it is an object of this invention to provide a method for enhancing the deposition of a polymeric coating on a denture.

It is a further object of this invention to provide a method, for using a denture bath comprising a liquid denture treating composition, to control the interaction of the denture with the air interface of the composition.

SUMMARY OF THE INVENTION

The invention provides a method for treating a denture, comprising:
a) soaking the denture in an aqueous composition comprising a polymeric coating agent having a surface tension in 0.1% aqueous solution of less than 37 mNm$^{-1}$ and a weight average molecular weight of 1,000 or greater, said composition having an interface with the surrounding air; and
b) passing the denture through the interface by draining the composition from a position beneath the denture or by lifting the denture through the interface.

The invention further relates to a method for coating a denture with a silicone or fluorocarbon polymer having a weight average molecular weight of 1,000 or greater, the method comprising the step of passing the denture through an interface between an aqueous composition comprising the polymer and the surrounding air, said interface having a rest surface area, whilst maintaining the surface area of the interface at about or below the rest surface area.

The invention yet further relates to use of a denture bath comprising:
a) an outer container for containing an aqueous composition;
b) means for supporting a denture in said container which allows said denture to be immersed in the aqueous composition; and
c) an aqueous composition comprising a silicone polymer having a weight average molecular weight of 1,000 or greater;
wherein the denture bath comprises a means for passing the denture through an interface of the aqueous composition with the surrounding air, said means being selected from means for draining the composition from a position beneath the denture and means for lifting the denture through the interface.

The methods enhance the coating of the denture with the polymer, thereby delivering improved plaque prevention.

All percentages and ratios herein are by weight, unless otherwise indicated.

DETAILED DESCRIPTION OF THE INVENTION

The methods herein are for treating a denture, especially by coating it. By "denture" is meant any device that is manufactured for placement within the mouth over a period of several days or more but that may be temporarily removed from it by the wearer for the purpose of cleaning or hygienic treatment. This includes artificial teeth and also orthodontic brackets, bridges and the like. The methods of treatment and coating herein take place outside of the mouth.

The methods of treatment comprise soaking the denture in an aqueous composition comprising an anti-plaque coating agent which is a polymer having a weight average molecular weight of about 1,000 or greater. The weight average molecular weight is preferably in the range from about 1,000 to 100,000, more preferably from about 2,000 to about 50,000 and especially from about 5,000 to about 20,000. To reduce the adherence of bacteria and other soils, the coating should have a low surface energy. Particularly preferred therefore are polymers or polymer mixtures having a surface tension in aqueous solution of less than about 37 mNm$^{-1}$, preferably less than about 32 mNm$^{-1}$, and more preferably less than about 30 mNm$^{-1}$. Surface tensions herein are measured at 25° C. in a 0.1% w/w solution of the polymer or polymer mixture in water using the Wilhelmy Plate method Preferred classes of polymers include polymers comprising silicone or fluorocarbon moieties. Homopolymers or copolymers can be used. The polymers are preferably liquid at 25° C. Preferred herein from the point of view of low toxicity, oral acceptability and/or cost and commercial availability are silicone polymers, especially those based on a siloxane backbone. Suitable classes of silicone polymers include, but are not limited to, dimethicones, dimethiconols, dimethicone copolyols and aminoalkylsilicones. Mixtures of suitable polymers can be used.

Preferred silicone polymers are dimethicone copolyol or aminoalkylsilicone antiplaque agents such as those described in WO 96/19563 and WO 96/19554.

above, preferably from about 5,000 to about 100,000, more preferably from about 5,000 to about 30,000. Aminoalkyl silicone compounds suitable for use herein are well known. Methods of preparing aminoalkylsilicones are given in, for example, U.S. Pat. No. 2,930,809. Examples of amodimethicones include OSi's Magnasoft® polymers which comprise aminoalkyl groups affixed to a predominantly polydimethylsiloxane structure. The typical structure of Magnasoft®'s aminoalkyl group-containing units is —OSi(Me)$C_3H_6$NH—$CH_2CH_2NH_2$.

Highly preferred for use herein are alkyl or alkoxy dimethicone copolyols having the formula (I):

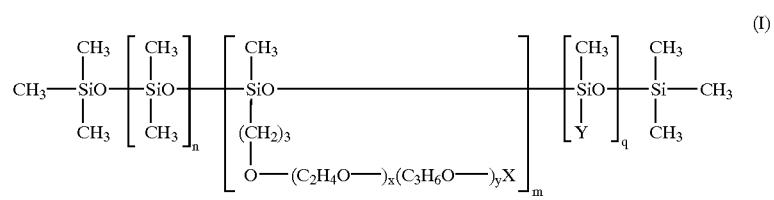

Suitable aminoalkylsilicones are selected from noncyclic, hydrophobic aminoalkylsilicones having a formula comprising two basic units:

1) $(R^1)_m(R)_n SiO_{(4-m-n)/2}$ wherein m+n is 1, 2 or 3; n is 1, 2 or 3; m is 0, 1, 2; and
2) $(R^1)_a(R^2)_b SiO_{(4-a-b)/2}$ wherein a+b is 1, 2, or 3, and a and b are integers, wherein $R^1$ and $R^2$ are independently selected from H, alkyl and alkenyl of about 1 to about 10 carbons optionally substituted with fluoro or cyano groups, hydroxy, alkoxy, and acetoxy, for example, wherein $R^1$ and $R^2$ are independently selected from methyl, ethyl, phenyl, vinyl, trifluoropropyl and cyanopropyl, and R is

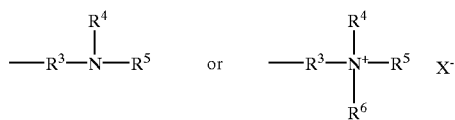

wherein $R^3$ is a divalent alkylene of about 1–20, preferably about 3–5 carbon atoms optionally substituted or interrupted by O atoms, $R^4$, $R^5$ and $R^6$ which may be the same or different are selected from H, alkyl of about 1–20, preferably about 1–10, more preferably about 1–4 carbons optionally substituted or interrupted by N and/or O atoms, and $X^-$ is a monovalent anion such as halide, hydroxide, and tosylate, said aminoalkyl-silicone including from about 0.1–2%, preferably from about 0.5–2% of unit (1) on a repeating unit basis. Preferred aminoalkylsilicones comprise amodimethicones. Amodimethicones are polydimethylsiloxane polymers containing aminoalkyl groups. The aminoalkyl groups may be present either pendant or at one or more ends of the polydimethylsiloxane chain. Preferred are aminoalkylsilicones in which aminoalkyl moiety R is selected from $(CH_2)_3NH_2$, $(CH_2)_3NHCH_2CH_2NH_2$, $(CH_2)_3N(CH_2CH_2OH)_2$, $(CH_2)_3NH_3^+X^-$, and $(CH_2)_3N(CH_3)_2(C_{18}H_{37})^+X^-$, and especially from $(CH_2)_3NH_2$ and $(CH_2)_3NHCH_2CH_2NH_2$. Also preferred are aminoalkyl silicones having an average molecular weight of about 5,000 and wherein X is selected from hydrogen, alkyl, alkoxy and acyl groups having from 1 to about 16 carbon atoms, Y is selected from alkyl and alkoxy groups having from about 1 to about 22 carbon atoms, n is from 0 to about 200, m is from about 1 to about 40, q is from 0 to about 100, the molecular weight of the residue $(C_2H_4O—)_x(C_3H_6O—)_yX$ is from about 50 to about 2000, and x and y are such that the weight ratio of oxyethylene:oxypropylene is from 100:0 to 0:100.

Particularly preferred are dimethicone copolyols wherein Y is selected from alkyl and alkoxy groups having from about 8 to about 22 carbon atoms, n is from 0 to about 200, m is from about 1 to about 40, q is from 1 to about 100, and the weight ratio of oxyethylene:oxypropylene is 100:0 to about 20:80, especially $C_{12}$ to $C_{20}$ alkyl dimethicone copolyols and more especially cetyl dimethicone copolyol which is marketed by Th. Goldschmidt AG under the Trade Name Abil® EM90.

Also preferred for use herein, especially in admixture with the $C_{12}$ to $C_{20}$ alkyl dimethicone copolyols above are polymeric silicone surfactants having the general formula (1) wherein X is selected from hydrogen, alkyl, alkoxy and acyl groups having from about 1 to about 16 carbon atoms, Y is $CH_3$, q is 0, n is from about 1 to about 100, m is from about 1 to about 40, the molecular weight of the residue $(C_2H_4O—)_x(C_3H_6O—)_yX$ is from about 50 to about 2000, and x and y are such that the weight ratio of oxyethylene:oxypropylene is from about 100:0 to about 0:100.

The silicone surfactant, itself a dimethicone copolyol, assists in dispersion and dissolution of the $C_{12}$ to $C_{20}$ alkyl dimethicone copolyols in aqueous media whilst still allowing them to deposit onto dentures. In preferred embodiments, the silicone surfactant is selected from dimethicone copolyols having a HLB value in the range from about 8 to about 14, more preferably from about 9 to about 12, and mixtures thereof. A suitable example of such a material is that marketed by OSi Specialities Inc. under the Trade Name Silwet® L7230. In general, the level of the silicone surfactant should be chosen such that the ratio of silicone surfactant to the $C_{12}$ to $C_{20}$ alkyl dimethicone copolyols is from about 0.5:1 to about 5:1, more preferably from about 0.8:1 to about 3:1, most preferably from about 0.9:1 to about 2:1 by weight.

The polymeric coating agent is generally present in a total level of from about 0.0001% to about 0.1%, preferably from about 0.001% to about 0.05%, more preferably from about 0.002% to about 0.02% by weight of the aqueous composition.

In preferred methods herein, the aqueous composition further comprises a persalt bleaching agent. The bleaching agent acts to clean and sterilise the denture before coating. Non-polymeric surfactants are also useful in this regard. The bleaching agent can be selected from any of the well-known bleaching agents known for use in denture cleansers such as the alkali metal and ammonium persulfates, perborates, percarbonates and perphosphates and the alkali metal and alkaline earth metal peroxides. Examples of suitable bleaching agents include potassium, ammonium, sodium and lithium persulfates and perborate mono- and tetrahydrates, sodium pyrophosphate peroxyhydrate and magnesium, calcium, strontium and zinc peroxides. Of these, however, the alkali metal persulfates, perborates and mixtures thereof are preferred for use herein, highly preferred being the alkali metal perborates.

Suitably, the aqueous composition is prepared by dissolution or dispersion in water of a concentrated composition such as a concentrated liquid, paste or a solid, granular or tablet composition which comprises the polymer and other adjuvants. In preferred embodiments herein the aqueous composition is prepared by dissolution in water of a tablet which effervesces on contact with water. Tablets provide a convenient unit dosage form and the effervescence helps disperse the tablet components.

The amount of bleaching agent in the tablet is generally from about 5% to about 70%, preferably from about 20% to about 60% by weight of the tablet. Preferred compositions comprise both a persulphate salt and a perborate salt. The persulphate salt and perborate salt can be in any ratio but it has been found that better foaming is achieved with a weight ratio of from about 0.8:1 to about 5:1, preferably from about 1.5:1 to about 4:1, more preferably from about 2:1 to about 3.5:1. Both of these ingredients are effective bleaches which contribute to the stain removal activity of the aqueous compositions.

Suitable sources of the persulphate salt are the alkali metal and ammonium persulphates. Preferred is potassium monopersulphate or a mixed salt thereof. Particularly preferred are the commercially available mixed salts such as Caroat®, marketed by Degussa, and Oxone®, marketed by E I du Pont de Nemours Co. and which are a 2:1:1 mixture of potassium monopersulphate, potassium sulphate and potassium bisulphate and which have an active oxygen content of about 4.5%. The level of persulphate salt is suitably from about 5% to about 60%, preferably from about 20% to about 50%, more preferably from about 35% to about 45% by weight of the tablet.

Suitable perborate salts are the alkali metal perborates, particularly sodium perborate. Sodium perborate is preferably used as the monohydrate or anhydrous form, although the tetrahydrate can also be used. Especially preferred is the monohydrate or mixtures of the monohydrate and anhydrous forms of sodium perborate. Suitably the ratio of anhydrous to monohydrate is from 0:100 to about 30:70. The total level of perborate salt is generally from about 6% to about 30%, preferably from about 10% to about 25%, more preferably from about 12% to about 18% by weight of the tablet.

A preferred method for incorporating the silicone polymer is via a spray-dried powder as will be described further below.

The powder includes a water-soluble carrier. By "water-soluble carrier" herein is meant any material which is a solid at 25° C., is capable of being processed into granular form, is capable of being made into a clear or translucent aqueous solution at 25° C. at a level of about 1% by weight of the solution, and is safe for use on human skin or mucosa. Suitable carriers include, but are not limited to, polyethylene glycols, starches, gum arabic, gum tragacanth, gum acacia, carrageenans, cellulose derivatives and mixtures thereof. Preferably, the carrier is capable of being spray-dried into a free-flowing powder. In especially preferred embodiments the water-soluble carrier is a food-grade carrier selected from starches, gum arabic, gum tragacanth, gum acacia and mixtures thereof. A particularly preferred carrier is a modified starch available under the tradename Capsul E from National Starch & Chemical of Manchester, UK. Optionally, the carrier can comprise a sugar alcohol or saccharide, such as sorbitol, mannitol or maltodextrin. Without being limited by theory, it is believed that the sugar alcohol or saccharide helps to form a film on the surface of the particle which improves the encapsulation of the oil by the powder particle. A preferred carrier consists of a mixture of starch and sorbitol, preferably from about 2.5:1 to about 4:1, more especially about 3:1 by weight of the carrier. A mixture of gum acacia and maltodextrin in the ratio of from about 1:2 to about 2:1 can also suitably be used.

The water-soluble carrier is generally present in a level of from about 50% to about 99%, preferably from about 60% to about 90%, more preferably from about 65% to about 90% by weight of the spray-dried powder.

The powders are generally in granular form, wherein the powder has a volume average particle size in the range from about 20 μm to about 500 μm, preferably from about 50 μm to about 250 μm, more preferably from about 80 μm to about 150 μm. The average particle size can be measured using standard sieve techniques well known in the art. Alternatively, the average particle size can be measured using a commercial instrument such as the Malvern Mastersizer X available from Malvern Instruments Ltd. of Malvern Worcs., UK,. The Mastersizer is preferably fitted with a MSX64 Dry Powder Feeder and a 300 mm lens for measuring particles in the range 1.2 to 600 microns.

The powders can be prepared by dispersing the silicone polymer(s) in a aqueous solution of the water-soluble carrier and spray-drying the resultant dispersion. Whilst, the strength of the carrier solution is not critical, it will be understood that very dilute solutions will require considerable input of energy to dry. Suitably the aqueous solution of the carrier will comprise from about 25% to about 50%, more preferably from about 30% to about 45%, more especially from about 35% to about 40% of the carrier by weight of the solution.

In order that the powder hereof has the desired properties, it is important to control the silicone droplet size within the dispersion. In general, the silicone should be present in the dispersion in the form of discrete droplets having a volume average droplet size in the range from about 0.5 μm to about 20 μm. Further, the ratio of the average spray-dried particle size to the average droplet size should be at least about 2.5:1. In preferred embodiments the ratio of the average spray-dried particle size to the average droplet size is at least about 4:1, preferably at least about 6:1, more preferably at least about 10:1. Smaller droplets, in relation to the final spray-dried powder particle size, serve to improve the flow characteristics and further processability of the powder. The desired droplet size can be achieved by using shear mixing to form the dispersion and measured by using phase contrast photomicroscopy. A suitable procedure is to use, for example, a Nikon Labophot 2 at 400× magnification with fixed focal length and fitted with a graticule. It will be appreciated that a suitable number of observations need to be made to reduce the sampling error. The precise number to be made will depend, for example, upon the droplet size distribution achieved. The dispersion is mixed, with adjustment of the shear rate if necessary, until the desired droplet size is attained.

The spray-dried silicone powders preferably also include a flavour or perfume oil. As used herein, the term 'flavour or perfume oil' means those flavour or perfume essences and equivalent synthetic ingredients which are added to the powder for the principal purpose of modifying the taste and/or odour or other organoleptic sensations of the powder or the final product into which the powder is incorporated. It excludes silicone polymers as described above but includes lipophilic physiological cooling agents.

Lipophilic flavorants suitable for use herein comprise one or more flavour components selected from wintergreen oil, oregano oil, bay leaf oil, peppermint oil, spearmint oil, clove oil, sage oil, sassafras oil, lemon oil, orange oil, anise oil, benzaldehyde, bitter almond oil, camphor, cedar leaf oil, marjoram oil, citronella oil, lavender oil, mustard oil, pine oil, pine needle oil, rosemary oil, thyme oil, cinnamon leaf oil, and mixtures thereof.

Physiological cooling agents suitable for use herein include carboxamides, menthane esters and menthane ethers, and mixtures thereof. Examples of preferred cooling agents suitable for use herein include Takasago 10 [3-1-menthoxy propan-1,2-diol (MPD)], from Takasago International Corporation, and carboxamides such as those described in U.S. Pat. No. 4,136,163, Jan. 23, 1979 to Watson et al., and U.S. Pat. No. 4,230,688, Oct. 28, 1980 to Rawsell et al.

The amount of flavour or perfume oil employed is normally a matter of preference subject to such factors as flavour type, base type and strength desired. The level of flavour or perfume oil in the compositions of the invention is generally in the range from about 1% to about 15% by weight of the spray-dried powder. Preferably the flavour or perfume oil is incorporated by making an intimate premix of the silicone polymer(s) and the flavour or perfume oil and then forming a dispersion of the premix in the carrier solution as described above.

It has been found that forming an intimate admixture of the flavour or perfume oil with the silicone polymer prior to dispersing the mixture in the aqueous carrier solution acts to reduce the droplet size of the dispersed oil and improve the flow characteristics and further processability of the powder.

It has further been found that the flavour or perfume oil being in intimate admixture with the silicone polymer acts to enhance the substantivity of the flavour or perfume oil to dentures, thereby providing enhanced and/or sustained organoleptic impact. In the same way, lipophilic antimicrobial compounds can advantageously be included along in the same manner as the flavour or perfume oil, to provide enhanced and/or sustained antimicrobial efficacy. Suitable lipophilic antimicrobial compounds for use herein include thymol, menthol, triclosan, 4-hexylresorcinol, phenol, eucalyptol, benzoic acid, benzoyl peroxide, butyl paraben, methyl paraben, propyl paraben, salicylamides, and mixtures thereof.

A preferred, but optional, component in the aqueous compositions of the present invention is a foam-forming surfactant selected from anionic surfactants, nonionic surfactants, amphoteric surfactants and mixtures thereof. The phrase 'foam-forming surfactant' as used herein excludes polymeric coating agents as described hereinbefore. The foam-forming surfactant used in the denture cleansing compositions of the invention can be selected from the many available that are compatible with the other ingredients of the aqueous compositions and tablets, both in the dry state and in solution.

Suitable anionic surfactants include alkyl sulphates, such as sodium lauryl sulphate, alkyl ether sulphates, alkyl aryl sulphonates such as sodium dodecyl benzene sulphonate (SDBS), alkyl sarcosinates, alkyl sulphoacetates and alkyl sulphosuccinates. A highly preferred anionic surface active agent is sodium lauryl sulphoacetate, commercially available as Lathanol® powder. It has also been found that the use of a surfactant mixture, comprising a primary surfactant and an additional co-surfactant, can boost foaming and reduce the total surfactant level. Suitably the total amount of foam-forming surfactant comprises from about 0.1% to about 3.8%, preferably from about 0.3% to about 2%, more preferably from about 0.5% to about 1.5% by weight of the tablet; suitable levels of co-surfactant are from about 0.1% to about 1%, preferably from about 0.2% to about 0.5% by weight of the tablet. If the total level of foam-forming surfactant is too high, then the tablets can become slow to dissolve. If the level is too low then foaming is impaired.

Suitable non-ionic and ampholytic surface active agents include, for example, condensation products of alkylene oxides such as ethylene or propylene oxide with fatty alcohols, phenols, fatty amines or fatty acid alkanolamides, the fatty acid alkanolamides themselves, esters of long-chained ($C_8$–$C_{22}$) fatty acids with polyalcohols or sugars, for example glycerylmonostearate or saccharose monolaurate or sorbitolpolyoxyethylene-mono-or di-stearate, betaines, sulphobetaines or long-chain alkylaminocarboxylic acids.

An important feature of the tablets of the present invention is that the silicone polymer and the foam-forming surfactant are in discrete, separate granules. By 'discrete, separate granules' is meant that the foam-forming surfactant is incorporated into a distinctly separate granule from the silicone polymer. It has been found that keeping foam-forming surfactant physically separate from the silicone polymer helps prevent the surfactant interfering with the silicone deposition process. One method for achieving this is to form a spray-dried powder comprising the silicone polymer, as described above and to either prepare a separate granular premix comprising the foam-forming surfactant, or to include the foam-forming surfactant with the excipients in the final mixing process prior to tabletting. It has been found that when the foam-forming surfactant is included with the excipients it can have a binding effect and eliminate or substantially reduce the need for additional binders such as polyethylene glycols which can have the effect of slowing down tablet disintegration.

Aqueous compositions of the invention can be supplemented by other usual components of such formulations, especially additional effervescence generators, bleach activators, desiccants, chelating agents, enzymes, flavours, physiological cooling agents, antimicrobial compounds, dyestuffs, sweeteners, tablet binders and fillers, foam stabilisers such as the fatty acid sugar esters, preservatives, lubricants such as talc, magnesium stearate, finely divided amorphous pyrogenic silicas, etc. The free moisture content of the tablet is desirably less than about 1% and especially less than about 0.5%.

The perborate salt/persulphate salt combinations described above give rise to oxygen effervescence. In preferred embodiments an additional, carbon dioxide effervescence generator comprising a bicarbonate salt and an acid is included in the tablets herein. The carbon dioxide effervescence generator is useful for providing rapid, initial effervescence when the tablet is first added to water which will usually be about neutral pH but may be slightly acidic. The initial effervescence is valuable for dispersing the tablet in water and assisting its dissolution by providing turbulence. Preferred bicarbonate salts are the rapidly soluble alkali metal bicarbonates, such as sodium bicarbonate, potassium bicarbonate and mixtures thereof, especially sodium bicarbonate. The bicarbonate salt is provided in admixture with at least one non-toxic, physiologically-acceptable organic or inorganic acid, such as tartaric, fumaric, citric, malic, maleic, gluconic, succinic, salicylic, adipic or sulphamic acid, sodium fumarate, sodium or potassium acid phosphates, betaine hydrochloride or mixtures thereof. Of these, sulphamic and malic acids are preferred.

In preferred tablet compositions, the carbon dioxide effervescence generator takes the form of a solid premix comprising sodium bicarbonate and sulphamic or malic acid, which in the presence of water releases carbon dioxide with effervescence. The premix can comprise further additives and excipients such as sodium carbonate and dye. Whilst sodium carbonate can itself can provide carbon dioxide effervescence, since it is not as soluble as the bicarbonate it is less valuable in this respect.

It has further been found that whilst it is valuable to have the bicarbonate salt present, too much carbon dioxide can lead to early foam collapse. For this reason the proportion of bicarbonate is preferably limited to well below that of the perborate salt so that oxygen effervescence predominates once the composition has started to fully dissolve. The weight ratio of the perborate salt to the bicarbonate salt, where both are used, is suitably in the range of from about 2:1 to about 20:1, preferably from about 2.5:1 to about 10:1, more preferably from about 3:1 to about 5:1.

Where used, the bicarbonate salt generally comprises from about 1% to about 20%, preferably from about 3% to about 10%, more preferably from about 4% to about 6% of the tablet. The acid component generally comprises from about 2% to about 15%, preferably from about 3% to about 10% of the tablet.

An especially preferred additional component of the compositions of the present invention is a bleach activator. Preferred bleach activators are described in detail in WO 96/19563.

The level of bleach activator by weight of the tablet is preferably from about 0.1% to about 10%, more preferably from about 0.5% to about 5%.

Tablet binders and fillers suitable for use herein include polyvinyl-pyrrolidone, poly (oxyethylene) of molecular weight 20,000 to 500,000, polyethyleneglycols of molecular weight of from about 1000 to about 50,000, Carbowax having a molecular weight of from 4000 to 20,000, fatty acids, sodium carboxymethyl cellulose, gelatin, fatty alcohols, clays, polymeric polycarboxylates, sodium carbonate, calcium carbonate, calcium hydroxide, magnesium oxide, magnesium hydroxide carbonate, sodium sulphate, proteins, cellulose ethers, cellulose esters, polyvinyl alcohol, alginic acid esters, and triglycerides. Of the above, polyethyleneglycols, especially those having molecular weight of from about 1,000 to about 30,000, preferably from about 12,000 to about 30,000, and triglycerides are highly preferred.

Chelating agents and enzymes can also optionally be used in the compositions of the present invention. Suitable chelating agents and enzymes are described in WO 96/19563.

An essential feature of the present invention is that the aqueous compositions to be employed in the methods herein have an interface with the air. Generally this will be arranged by preparing the composition in a beaker or similar open container as is usually the case for denture cleansing compositions. Thus if the aqueous composition part-fills a glass beaker, the upper surface of the composition is in contact with the air and is the air interface. The air interface should clearly be of such dimensions that the denture can be passed through it, for example by lifting out a denture which is immersed in the composition. Once the denture is in the composition the container can optionally be loosely covered or even sealed until such time the denture is to be removed.

The air interface has a rest surface area, which is the area of the air interface when the aqueous composition is static and before the denture is passed through it. This can be before immersion of the denture in the composition, such as when a denture cleansing tablet is dissolved in a glass of water before adding the denture. Alternatively it may be, for example, that the denture is already immersed in a glass of water before a tablet is added to prepare the aqueous composition. Yet again, the denture and the tablet can be placed in the empty container which is then filled or part-filled with water to prepare the aqueous composition; the rest surface area is attained after all the water has been added. Preferably the volume and depth of the aqueous composition is such that the denture can be fully immersed with no part of it projecting through the air interface in the rest state. A typical volume for an aqueous composition of the present invention is from about 100 to 500 ml, more usually from about 150 to about 350 ml. The rest surface area of the composition is generally in the range from about 20 to about 100, more usually from about 40 to about 70 $cm^2$.

The denture is preferably allowed to soak for a period of from one minute to twenty-four hours, preferably from ten minutes to twelve hours and more preferably for about fifteen minutes.

It is preferred that the area of the interface be maintained at about or below its rest surface area whilst the denture is passed through it. For the purposes of this invention, the area of the interface whilst the denture is being passed through it does not include that portion which is in contact with the denture, such as residual composition which is still draining from the denture. A small increase of, say, 5% or less in the surface area, which may be due to some small turbulence at the interface whilst the denture is removed, can be tolerated. Much larger increases in surface area can result if the glass or other container for the composition is tipped to remove the composition. For this reason, and to avoid loss of the polymer rich surface layer of the composition before it has had a chance to contact the denture, it is preferred not to tip the container for the composition whilst the denture is being passed through its air interface. This can be arranged by draining the composition from a position beneath the denture or by lifting the denture through the interface. Preferably the denture is passed through the interface by being lifted through it.

The outer container can be any suitable container, such as a cup or drinking glass, which is capable of holding the aqueous composition, without reacting with it, and into and from which the denture can be placed and removed. The container is preferably made of plastic. Generally the container will have a base and one or more peripheral walls. The means for supporting the denture can be as simple as the base of the container or it may be a separate cradle which can be lowered into the outer container which allows the aqueous composition to drain away from the cradle the denture it supports when it is raised to remove the denture. The container can have a draining means, such as a tap or valve in its base, which allows the composition to be drained from a position beneath the denture. In this case the air interface will lower within the outer container as the composition is drained. In preferred embodiments herein the denture bath is purpose designed with an outer container having a closed base and a peripheral wall of circular cross-section. The peripheral wall has an upper peripheral rim.

After being passed through the air interface of the composition the denture is preferably rinsed with water and brushed. It has been found that this helps improve the uniformity of coating and/or orients the polymer molecules within the coating to improve resistance to plaque build-up.

The invention will now be described by way of example only, and with reference to the accompanying drawings in which.

EXAMPLE

The following are representative denture cleanser tablets according to the invention. The percentages are by weight of the denture cleanser tablet.

Figure 1:
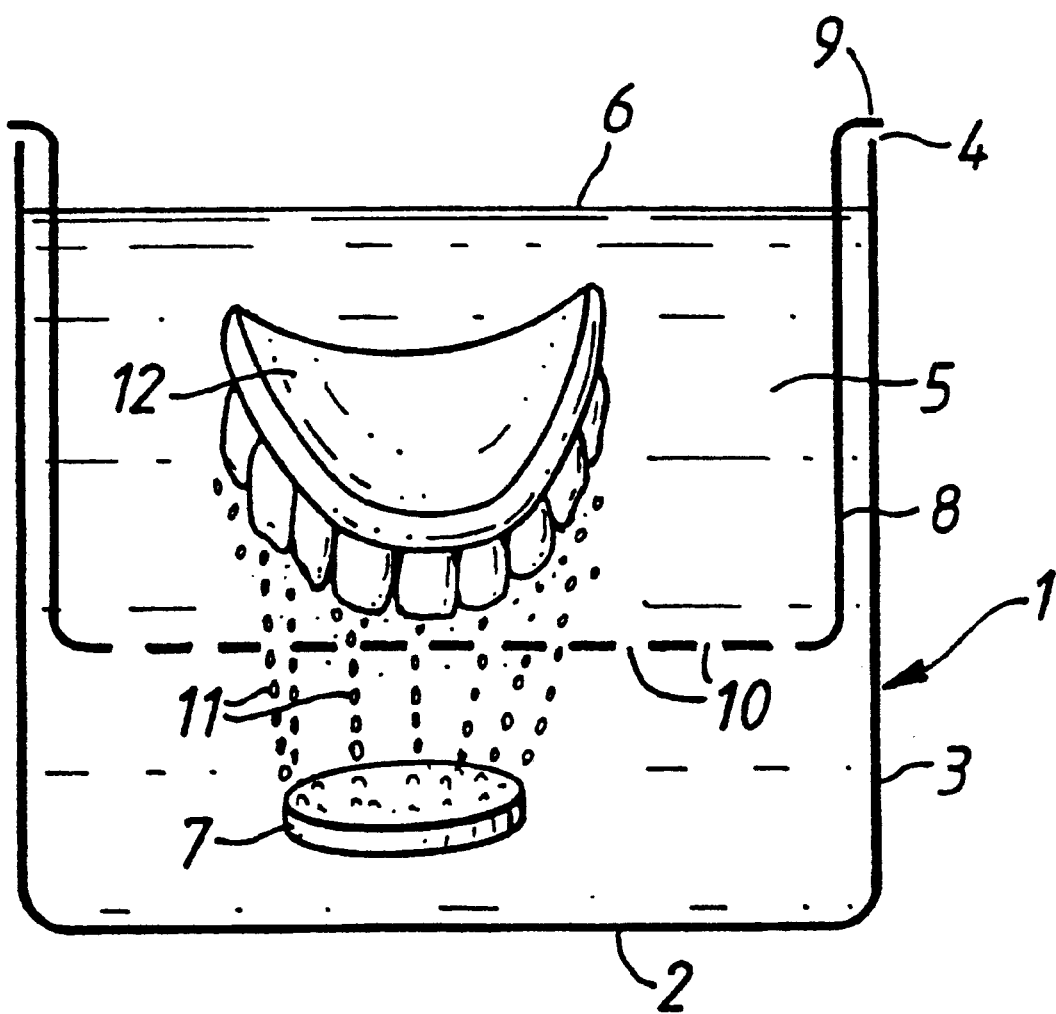
FIG. 1 is a vertical cross-section through a denture bath suitable for use in the methods of the present invention.

In FIG. 1, a denture bath comprises an outer container 1 having a base 2 and peripheral wall 3 of generally cylindrical cross-section. The peripheral wall has an upper peripheral rim 4. The outer container contains an aqueous composition 5 having an air interface 6. The aqueous composition is prepared by adding 250 ml water into the outer container after placing 3 g denture cleanser tablet 7 and then inner basket 8, supporting denture 12, into the container. The tablet comprises a silicone polymer, a persalt bleaching agent and other additives, including an effervescent system, exemplified in more detail below. The inner basket 8 which has a formed rim 9 is supported on the upper peripheral rim 4 of the outer container and has holes 10 formed in its base. The holes allow liquid communication between the outer container and the interior of the basket. When the water is added the tablet dissolves with effervescence generating bubbles 11 of oxygen and carbon dioxide which help the tablet disintegrate and carry the actives in the tablet to the denture. The outer container can optionally be covered with a lid (not shown) which prevents dust and the like from falling into the aqueous composition. The denture is allowed to soak in the aqueous composition for a period of fifteen minutes and is then removed by lifting out basket 8 from the outer container. The holes in the base of the basket allow the aqueous composition to drain away from the denture. As the basket is lifted it causes denture 12 to pass through interface 6.

Figure 2:
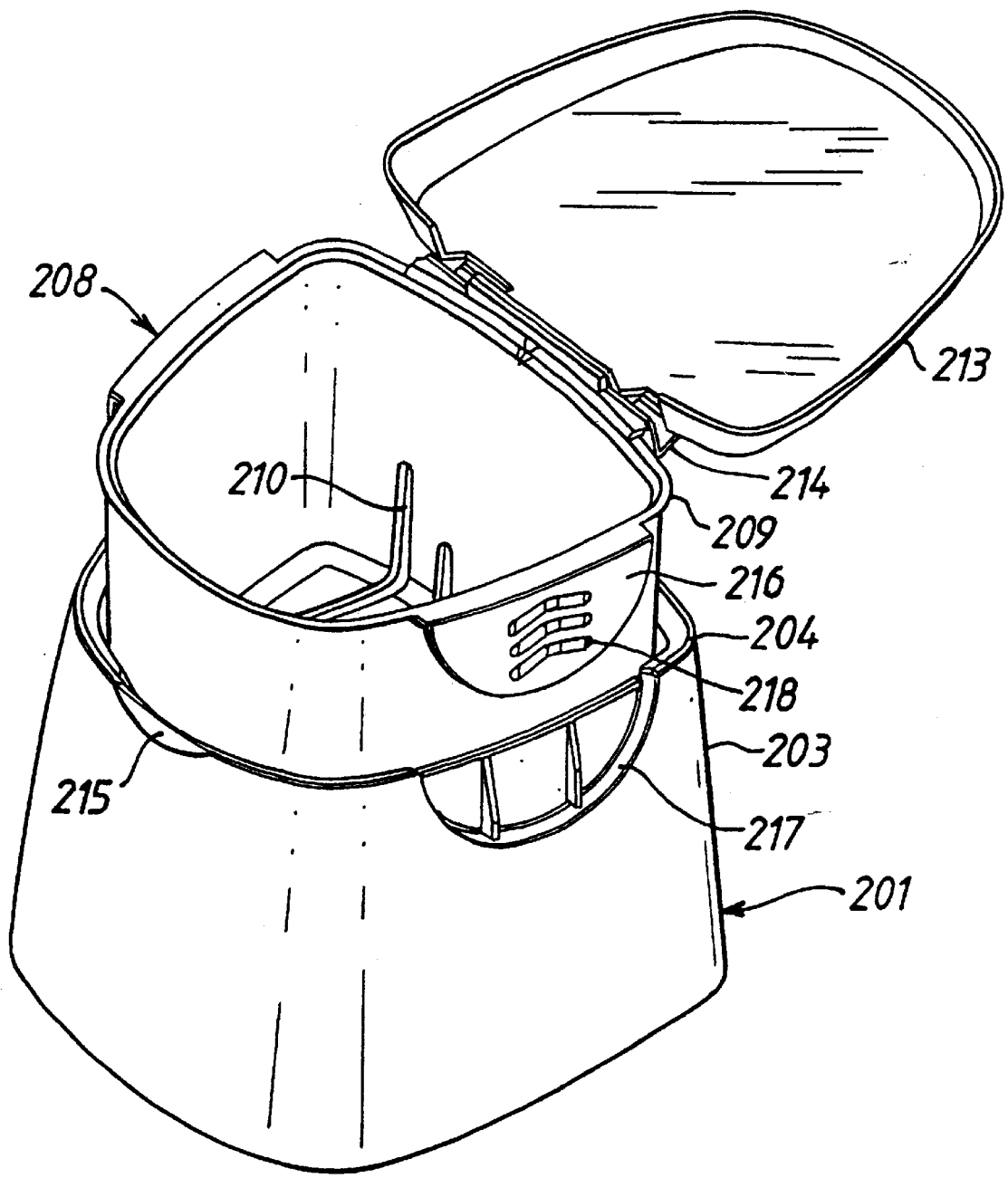
FIG. 2 is a perspective view of a further embodiment of a denture bath, comprising an outer container and a basket, suitable for use in the methods of the present invention. The figure shows the basket partially inserted into the outer container.

FIG. 2 shows a further embodiment of a denture bath suitable for use in the methods of the present invention. The bath comprises an outer container 201 and an inner basket 208. The outer container has a base (not shown) and peripheral wall 203, the wall having an upper peripheral rim 204. The outer container is able to contain an aqueous composition having an air interface. The inner basket 208 which has a formed rim 209 is supported on the upper peripheral rim 204 of the outer container and has holes 210 formed in its base, in the form of elongated slots. The dimensions of the container and the basket are such that, when the basket is fully inserted into the container, there is a clearance between the base of the basket and the base of the container sufficient to accommodate a denture cleansing tablet, as generally shown in FIG. 1. The slots in the basket 208 allow liquid communication between the outer container 201 and the interior of the basket. The basket 208 further comprises a lid 213 which articulates on the basket via two living hinges 214. When the basket is fully inserted into the outer container and lid 213 is closed, the lid completely covers container 201. An undercut 215 on the outer wall of the container assists the user in lifting the lid, if required, whilst the basket is inserted in the container. A preferred method of removing the basket from the container, when the container holds an aqueous composition according to the invention, is to lift the basket without opening the lid. When used in this way the aqueous composition drains through the slots at the bottom of the basket, and the denture passes through the air interface of the composition. With the lid closed, the temptation to decant the composition via the open top of the bath is removed. To further assist removal of the basket in this manner, the basket is provided with grip tabs 216. In this embodiment the tabs depend from extensions of formed rim 209 and lie approximately parallel to the side wall of the basket. The tabs 216 mate with corresponding recesses 217 in outside of the peripheral wall 203 of the container, so that when the basket is fully inserted into the container the tabs fit flush with the container peripheral wall. The tabs can optionally be provided with undercuts or surface decoration, such as the chevrons 218 indicated, to provide additional grip and/or to indicate the direction of removal of the basket. The internal dimensions of the container are such that, when the basket is fully inserted and contains a full denture, a volume of the composition in the range from about 130 to about 185 mls will fully cover the denture, depending on its size. The internal dimensions of the container and the basket are preferably such that a denture can be placed in the basket in a horizontal configuration, that is with the outer surfaces of the teeth facing to the peripheral wall of the container, as generally indicated in FIG. 1. The horizontal orientation of the denture indicated is preferred for optimum coating of the teeth with the polymeric treatment agent. Good coating of the front teeth of a denture can also be obtained when the denture is placed vertically in the basket, with the front teeth facing upwards, however this orientation generally requires a larger volume of the aqueous cleansing composition to cover the denture. The holes in the base of basket 208 can be of any size and shape provided that they allow liquid communication between the outer container 201 and the interior of the basket 208. Preferably they are such that, as the cleansing tablet dissolves with effervescence, the aqueous composition being formed will be relatively unobstructed by the material of the basket. Preferably also the surface area of the basket is kept low to avoid undue competition with the denture for the polymeric treatment agent. In practice, there also needs to be sufficient material in the basket to give it sufficient rigidity to retain its shape. A suitable compromise has been found to be where the ratio of surface area of the supporting material of the base to the surface area of the holes in the base is in the range from about 2:1 to 1:2.

The tablet can be of various compositions such as formulations A–C below in which the blue and white granulates are made separately by roller compaction. The silicone polymer-containing spray-dried powder is made as described hereinbefore. The granulates, the spray-dried powder and the excipients are then mixed together in a planetary mixer and 3 g tablets are made by compressing the mixture of components in a punch and dye rotary tabletting press at a pressure of about $2 \times 10^5$ kPa.

References used in the following table are as follows.
[1] Caroat®.
[2] Cetyl dimethicone copolyol from Goldschmidt.
[3] Dimethicone copolyol from OSi Specialities Inc.
[4] Modified starch from National Starch & Chemical
[5] Mixture of hardened triglycerides from soya oil, available from Ingelheim Boehringer

|  | A % | B % | C % |
|---|---|---|---|
| WHITE GRANULATE |  |  |  |
| Potassium monopersulphate salt[1] | 25.54 | 42.66 | 50.40 |
| Sodium carbonate | 6.82 | 7.45 | 7.91 |
| Tetrasodium EDTA | 0.20 | 0.47 | 0.49 |
| Lathanol ® powder | — | — | 3.40 |
| TOTAL WHITE GRANULATE | 32.56 | 50.58 | 62.20 |
| BLUE GRANULATE |  |  |  |
| Sodium carbonate | 3.02 | 0.78 | 0.82 |
| Sulphamic acid | 1.51 | 4.88 | 5.19 |
| Sodium bicarbonate | 2.2 | 4.67 | 1.1 |
| Blue dye | 0.11 | 0.21 | 0.33 |
| TOTAL BLUE GRANULATE | 6.84 | 10.54 | 7.44 |
| SPRAY-DRIED POWDER |  |  |  |
| Abil ® EM 90[2] | 1.5 | 1.13 | 0.41 |
| Silwet ® L7230[3] | 5.33 | 1.4 | 0.15 |
| Peppermint flavour oil | 1.91 | 1.23 | 0.45 |
| Capsul E[4] | 5.59 | 6.55 | 6.1 |
| Sorbitol | 0.6 | 2.18 | 0.92 |
| Fumed Silica | 0.66 | 0.13 | 2.00 |
| TOTAL SPRAY-DRIED POWDER | 15.59 | 12.62 | 10.03 |
| EXCIPIENTS |  |  |  |
| TAED | 3.08 | 2.33 | 1.75 |
| Sodium perborate monohydrate | 18.75 | 15.51 | 11.10 |
| Lathanol ® powder | 0.55 | 0.97 | — |
| Sodium carbonate | 18.5 | 5.78 | 3.96 |
| Fumed silica | 0.39 | 0.58 | 0.62 |
| Hydrated silica | 0.29 | 0.31 | 0.33 |
| Boeson VP 60[5] | 0.1 | 0.78 | 0.82 |
| Spray-dried peppermint oil | 3.35 | 0 | 1.75 |
| TOTAL WHITE EXCIPIENTS | 45.01 | 26.26 | 20.33 |
|  | 100 | 100 | 100 |

What is claimed is:

1. A denture bath comprising:
   a) an outer container for containing an aqueous composition;
   b) an aqueous composition comprising a polymeric coating agent having a surface tension in 0.1% aqueous solution of less than 37 mNm$^{-1}$ and a weight average molecular weight of 1,000 or greater; and
   c) means for supporting a denture in the container, which means allows the denture to be immersed in the aqueous composition; and
   wherein the denture bath further comprises a means for passing the denture through an interface of the aqueous composition with the surrounding air, the means being selected from means for draining the composition from a position beneath the denture and means for lifting the denture through the interface.

2. A denture bath according to claim 1, wherein the outer container comprises a base and one or more peripheral walls having an upper peripheral rim, the one or more peripheral walls oriented in a substantially perpendicular direction with respect to the base.

3. A denture bath according to claim 2, wherein the one or more peripheral walls have a generally cylindrical cross-section.

4. A denture bath according to claim 2, wherein the outer container further comprises a lid.

5. A denture bath according to claim 1, wherein the outer container is plastic.

6. A denture bath according to claim 1, wherein the supporting means comprises a basket supported in the container, the basket having a base with holes formed therein to allow liquid passage through the base of the basket.

7. A denture bath according to claim 1, wherein the polymeric coating agent is a silicone polymer.

8. A denture bath according to claim 7, wherein the silicone polymer is of the general formula (I):

wherein X is selected from hydrogen, alkyl, alkoxy and acyl groups having from 1 to about 16 carbon atoms, Y is selected from alkyl and alkoxy groups having from about 1 to about 22 carbon atoms, n is from 0 to about 200, m is from about 1 to about 40, q is from 0 to about 100, the molecular weight of the residue $(C_2H_4O-)_x(C_3H_6O-)_y X$ is from about 50 to about 2000. and x and y are such that the weight ratio of oxyethylene:oxypropylene is from 100:0 to 0:100.

9. A denture bath according to claim 8, wherein the silicone polymer is cetyl dimethicone copolyl.

10. A denture bath according to claim 1 wherein the aqueous composition further comprises a persalt bleaching agent.

11. A denture bath comprising:

(a) an outer container containing an aqueous composition comprising a polymeric coating agent having a surface tension in 0.1% aqueous solution of less than 37 mNm$^{-1}$ and a weight average molecular weight of 1,000 or greater, wherein the aqueous composition has an air interface; and (b) a cradle adapted to support a denture in the outer container and adapted to allow the denture to be immersed in the aqueous composition;

wherein the denture bath is configured to allow the denture to pass through the air interface.

12. A denture bath according to claim 11, wherein the outer container is provided with an opening configured to allow the cradle to be removed from the container and to allow the denture to be passed through the air interface by lifting the cradle from the container.

13. A denture bath according to claim 11, wherein the outer container is provided with a draining valve at a position below the cradle, whereby the denture is passed through the air interface by draining the aqueous composition.

14. A denture bath according to claim 11, wherein the polymeric coating agent is a silicone polymer.

15. A denture bath according to claim 14, wherein the silicone polymer is of the general formula (I):

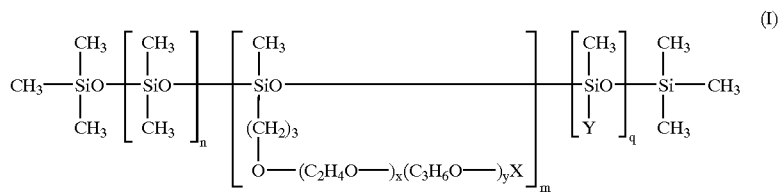

wherein X is selected from hydrogen, alkyl, alkoxy and acyl groups having from 1 to about 16 carbon atoms, Y is selected from alkyl and alkoxy groups having from about 1 to about 22 carbon atoms, n is from 0 to about 200, m is from about 1 to about 40, q is from 0 to about 100. the molecular weight of the residue $(C_2H_4O-)_x(C_3H_6O-)yX$ is from about 50 to about 2000, and x and y are such that the weight ratio of oxyethylene:oxypropylene is from 100:0 to 0:100.

16. A denture bath according to claim 15, wherein the silicone polymer is cetyl dimethicone copolyl.

17. A denture bath according to claim 11, wherein the aqueous composition further comprises a persalt bleaching agent.

* * * * *

UNITED STATES PATENT AND TRADEMARK OFFICE
CERTIFICATE OF CORRECTION

PATENT NO.    : 6,610,149 B2
DATED         : August 26, 2003
INVENTOR(S)   : Mark Ieuan Edwards et al.

It is certified that error appears in the above-identified patent and that said Letters Patent is hereby corrected as shown below:

Column 14,
Line 20, insert the following formula (I):

--

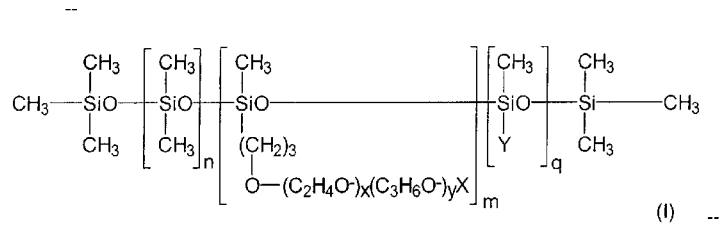

(I) --

Signed and Sealed this

Twenty-fourth Day of February, 2004

JON W. DUDAS
*Acting Director of the United States Patent and Trademark Office*